United States Patent
Inoue

(10) Patent No.: US 9,511,205 B2
(45) Date of Patent: Dec. 6, 2016

(54) CATHETER-TYPE THERAPEUTIC OR DIAGNOSTIC INSTRUMENT PROVIDED WITH SHAPED WIRE MEMBERS AND CATHETER TUBE TO BE USED TOGETHER WITH SHAPED WIRE MEMBERS

(71) Applicant: PTMC INSTITUTE, Kyoto-shi, Kyoto (JP)

(72) Inventor: Kanji Inoue, Kyoto (JP)

(73) Assignee: PTMC Institute, Kyoto-shi (JP)

( * ) Notice: Subject to any disclaimer, the term of this patent is extended or adjusted under 35 U.S.C. 154(b) by 69 days.

(21) Appl. No.: 14/406,745

(22) PCT Filed: Jul. 1, 2013

(86) PCT No.: PCT/JP2013/068061
§ 371 (c)(1),
(2) Date: Dec. 9, 2014

(87) PCT Pub. No.: WO2014/007221
PCT Pub. Date: Jan. 9, 2014

(65) Prior Publication Data
US 2015/0141855 A1 May 21, 2015

(30) Foreign Application Priority Data
Jul. 5, 2012 (JP) .................................. 2012-151917

(51) Int. Cl.
*A61M 29/00* (2006.01)
*A61M 25/01* (2006.01)
(Continued)

(52) U.S. Cl.
CPC ...... *A61M 25/0152* (2013.01); *A61B 5/02007* (2013.01); *A61B 5/02028* (2013.01);
(Continued)

(58) Field of Classification Search
CPC .................. A61M 25/0041; A61M 2025/004; A61M 2025/0161; A61M 2029/025; A61M 2210/127; A61M 25/0026; A61M 25/0032; A61M 25/0102; A61M 25/0147; A61M 25/0152; A61B 18/1492; A61B 2017/00243; A61B 2017/003; A61B 5/6853; A61B 5/6855
USPC ................ 600/435, 481, 508, 585; 604/532; 606/129
See application file for complete search history.

(56) References Cited

U.S. PATENT DOCUMENTS 2,118,631 A * 5/1938 Wappler .......... A61M 25/09033
15/104.33
5,299,574 A 4/1994 Bower
(Continued)

FOREIGN PATENT DOCUMENTS

JP 63353 1/1994
JP 824341 A 1/1996
(Continued)

OTHER PUBLICATIONS

"Soboben Koren Sekkaijutsu (PTMC) no Kaihatsu," Shinzo, vol. 39, No. 1, pp. 57-68, Jan. 2007, 13 pages.
(Continued)

*Primary Examiner* — Katherine M Shi
(74) *Attorney, Agent, or Firm* — Alleman Hall McCoy Russell & Tuttle LLP

(57) ABSTRACT

A therapeutic or diagnostic instrument includes first and second shaped wire members and that can be simultaneously inserted into a catheter tube and has predetermined bending elasticity, in which the first and second shaped wire members and are adapted to respectively have first and second curving parts that curve in a natural state, and when inserted into the catheter tube, curve the catheter tube at two desired positions correspondingly with the first and second curving parts.

2 Claims, 17 Drawing Sheets

(51) Int. Cl.
  *A61B 5/02* (2006.01)
  *A61B 5/00* (2006.01)
  *A61M 25/09* (2006.01)
  *A61M 29/02* (2006.01)
  *A61M 25/00* (2006.01)

(52) U.S. Cl.
  CPC ........... *A61B5/6853* (2013.01); *A61B 5/6855* (2013.01); *A61M 25/0026* (2013.01); *A61M 25/0041* (2013.01); *A61M 25/0102* (2013.01); *A61M 25/09* (2013.01); *A61M 29/02* (2013.01); *A61M 25/0032* (2013.01); *A61M 2025/004* (2013.01); *A61M 2029/025* (2013.01); *A61M 2210/127* (2013.01)

(56) References Cited

U.S. PATENT DOCUMENTS

| | | | | |
|---|---|---|---|---|
| 5,415,636 | A | * | 5/1995 | Forman ............... A61M 25/104 604/101.03 |
| 5,807,324 | A | * | 9/1998 | Griffin, III ......... A61B 18/1492 604/264 |
| 2009/0105724 | A1 | | 4/2009 | Yoshizaki et al. |
| 2010/0168511 | A1 | * | 7/2010 | Muni ................ A61M 25/0152 600/104 |
| 2010/0179562 | A1 | * | 7/2010 | Linker ................. A61N 1/0551 606/129 |
| 2010/0217261 | A1 | | 8/2010 | Watson |

FOREIGN PATENT DOCUMENTS

| JP | 2003509087 A | 3/2003 |
|---|---|---|
| JP | 2007130116 A | 5/2007 |
| JP | 2008246203 A | 10/2008 |
| JP | 4680007 B2 | 5/2011 |
| WO | 9505192 A1 | 2/1995 |
| WO | 2004105599 A1 | 12/2004 |
| WO | 2007026555 A1 | 3/2007 |
| WO | 2010083308 A1 | 7/2010 |
| WO | 2010096347 A1 | 8/2010 |
| WO | 2013166471 A1 | 11/2013 |

OTHER PUBLICATIONS

Ikegami Hospital Document, www.ikegamihosp.jp/bumon/shinryou/pdf/PTAV.pdf, Available as early as Oct. 25, 2011, 2 pages.
ISA Japanese Patent Office, International Search Report Issued in Application No. PCT/JP2013/068061, Aug. 6, 2013, WIPO, 7 pages.
State Intellectual Property Office of the People's Republic of China, Office Action Issued in Application No. 201380029132.0, Jan. 29, 2016, 8 pages.
European Patent Office, Partial Supplementary European Search Report Issued in Application No. 13813232.9, May 30, 2016, Germany, 6 pages.
European Patent Office, Extended European Search Report Issued in Application No. 13813232.9, Sep. 15, 2016, Germany, 12 pages.

* cited by examiner

CATHETER-TYPE THERAPEUTIC OR DIAGNOSTIC INSTRUMENT PROVIDED WITH SHAPED WIRE MEMBERS AND CATHETER TUBE TO BE USED TOGETHER WITH SHAPED WIRE MEMBERS

TECHNICAL FIELD

The present invention relates to a catheter-type therapeutic or diagnostic instrument that is adapted to be attached with a balloon at the fore end of a catheter tube, and inserted into a cardiac blood vessel for use in therapy for valve stenosis, or the like.

BACKGROUND ART

It has been reported that therapy using a balloon catheter is effective for aortic valve stenosis. For example, Non Patent Literature 1 describes advancing an Inoue balloon to the aortic valve position while making a guide wire, which has been made to pass in the order of the right atrium, left atrium, left ventricle, aortic valve, and aorta, guide the Inoue balloon, and in this position, sufficiently dilating and forming the valve.

However, this surgical operation requires skill because the catheter and guide wire are difficult to operate. For example, it is necessary to loop the guide wire 360 degrees or more inside the heart; moreover, an operation to loop the guide wire is extremely difficult. Also, it is not easy to insert the catheter tube along the looped guide wire. In particular, the left ventricle is relatively small, and in the left ventricle, the guide wire makes a sharp curve, so that the catheter tube may not advance in the left ventricle. Further, when pulling the guide wire and catheter tube in order to take them out, because the catheter tube is looped 360 degrees, a situation may arise where the loop only decreases in size as if a knot is tightened, and the fore end of the catheter tube does not move, potentially damaging the valve.

CITATION LIST

Non Patent Literature

Non Patent Literature 1: www.ikegamihosp.jp/bumon/shin-ryou/pdf/PTAV.pdf

SUMMARY OF INVENTION

Technical Problem

The present invention is made in consideration of such possible problems, and a main intended object thereof is to provide a catheter-type therapeutic or diagnostic instrument that makes it possible to simply, surely, and more safely perform an operation for the insertion of a catheter tube where it is necessary to loop the catheter tube, such as in the case of a cardiac blood vessel.

Solution to Problem

That is, the therapeutic or diagnostic instrument according to the present invention includes a catheter tube to be inserted into the body, and first and second shaped wire members that can be simultaneously inserted into the catheter tube and have predetermined bending elasticity, in which the first shaped wire member has a first curving part that curves in a natural state, and when inserted into the catheter tube, curves the catheter tube correspondingly with the first curving part, and the second shaped wire member has a second curving part that curves in the natural state, and when inserted into the catheter tube, curves the catheter tube correspondingly with the second curving part.

Such a configuration makes it possible to curve the catheter tube at two desired positions by operating the two shaped wire members back and forth, without the aid of a guide wire, so that the catheter tube can be looped in order to make the catheter tube pass through, for example, each valve in a cardiac blood vessel, and operability when looping the catheter tube is significantly improved, enabling a surgical operation to be easily and surely performed.

Also, a curved shape of the catheter tube can be controlled with the shaped wire members, and therefore the catheter tube can be easily removed along substantially the same path as a path for advancement. Accordingly, even in the case where the catheter tube is looped, when removing the catheter tube, a diameter of the loop can be reduced to surely prevent a situation of damaging a valve or the like.

In order to further improve the operability of the catheter tube, the instrument is preferably configured such that a degree of curvature is different between the first and the second curving parts of the shaped wire members.

As a specific embodiment making the effects of the present invention more remarkable, one that is inserted into a cardiac blood vessel for use in therapy for cardiovascular disease can be cited.

As a preferred embodiment, a balloon catheter attached with a balloon at the fore end of the catheter tube can be cited.

In order to make it possible to simultaneously insert the two shaped wire members into the catheter tube, and smoothly operate both of them back and forth, the instrument is desirably configured such that: for example, the catheter tube has a double tube structure having an outer tube and an inner tube for inserting a guide wire; the second shaped wire member is inserted into the inner tube; and the first shaped wire member is inserted between the outer tube and the inner tube.

In order to surely prevent the first shaped wire member from protruding from the catheter tube, the instrument is preferably configured such that a wire member insertion tube of which the fore end is sealed is placed between the outer tube and the inner tube, and the first shaped wire member is inserted into the wire member insertion tube.

In order to improve operability inside a cardiac blood vessel, the instrument is preferably configured such that the first curving part and the second curving part can curve the catheter tube approximately 270 to 360 degrees.

In order to expand an applicable scope to therapies and diagnoses of various sites as well as further improving the operability, preferably, a first shaped wire member has a first curving part of which a degree of curvature can be changed by an operation performed by hand at the rear end of the catheter tube.

Note that preferably, the first curving part in this case is not at a fixed position but adapted to be changeable by an operation performed by hand at the rear end of the catheter tube.

In order to use such a therapeutic or diagnostic instrument to make the catheter tube reach the aortic valve using an antegrade approach, it is preferable to undergo the following steps of:

(1) making the fore end part of the catheter tube penetrate through the interatrial septum from the right atrium and reach the left atrium;

(2) inserting the first shaped wire member and the second shaped wire member into the catheter tube to form a first curved part at the fore end part of the catheter tube with the first curving part as well as forming a second curved part, which is curved more gently than the first curved part, on the base end side beyond the first curved part of the catheter tube with the second curving part;

(3) advancing the catheter tube, and making the catheter tube pass through the mitral valve with the first curved part being at the head and reach the left ventricle in a position where the fore end of the catheter tube faces the aortic valve (to facilitate such an operation, the second shaped wire member and the corresponding second curving part curve the catheter tube 180 degrees, the catheter tube advancing from the inferior vena cava to the head side is directed through the right atrium to the mitral valve positioned in the tail side direction in the left atrium, and the catheter tube is made to pass through the mitral valve by a push-pull operation); and (4) advancing the catheter tube, and making the catheter tube pass through the aortic valve from the fore end part of the catheter tube (to facilitate such an operation, the first curving part corresponding to the first shaped wire member is placed near the left ventricular apex, and the catheter tube is pushed forward and made to pass through the aortic valve).

Also, in order to prevent the catheter tube after the insertion from making an unexpected movement, and surely fix the catheter tube, in a state where the fore end part of the catheter tube has passed through the aortic valve, the second shaped wire member is removed, and instead, the guide wire is inserted into the catheter tube and made to pass through the aortic valve, after which the fore end part of the guide wire is made to reach the descending aorta.

Note that in step (1), the catheter tube can also be inserted into the body in a state where at least one of the shaped wire members (preferably the first shaped wire member) is inserted into the catheter tube.

The medical instrument according to the present invention can be configured even with one shaped wire member. Desirably, the shaped wire member in such a case has: a first curving part that curves in a natural state; and a second curving part that curves so as to have a degree of curvature different from the first curving part, and when inserted into the catheter tube, curves the catheter tube at two positions correspondingly with the first curving part and the second curving part.

A catheter tube according to the present invention is disclosed, which includes: a guide wire insertion tube for inserting a guide wire and a wire member insertion tube for inserting the shaped wire member, and when inserted with the shaped wire member, is curved correspondingly by the curving part. Such a configuration makes it possible to smoothly operate the shaped wire member back and forth through the wire member insertion tube.

Also, another embodiment is disclosed, which includes: an outer tube; an inner tube for inserting a guide wire; and a wire member insertion tube placed between the outer tube and the inner tube.

Note that in the case where there are multiple shaped wire members, multiple wire member insertion tubes may be provided correspondingly for a number of the shaped wire members.

Advantageous Effects of the Invention

According to the present invention configured as described, by operating the shaped wire members back and forth, the catheter tube can be curved at two desired positions, so that without the aid of a guide wire, the catheter tube can be looped in order to make the catheter tube pass through, for example, each valve in a cardiac blood vessel, and operability when looping the catheter tube is significantly improved, enabling a surgical operation to be easily and surely performed.

Also, a curved shape of the catheter tube can be controlled with the shaped wire members, and therefore the catheter tube can be easily removed along substantially the same path as a path for advancement. Accordingly, even in the case where the catheter tube is looped, when removing the catheter tube, a diameter of the loop can be reduced to surely prevent any potential damage to a valve or the like.

REFERENCE CHARACTER LIST

Figure 1:
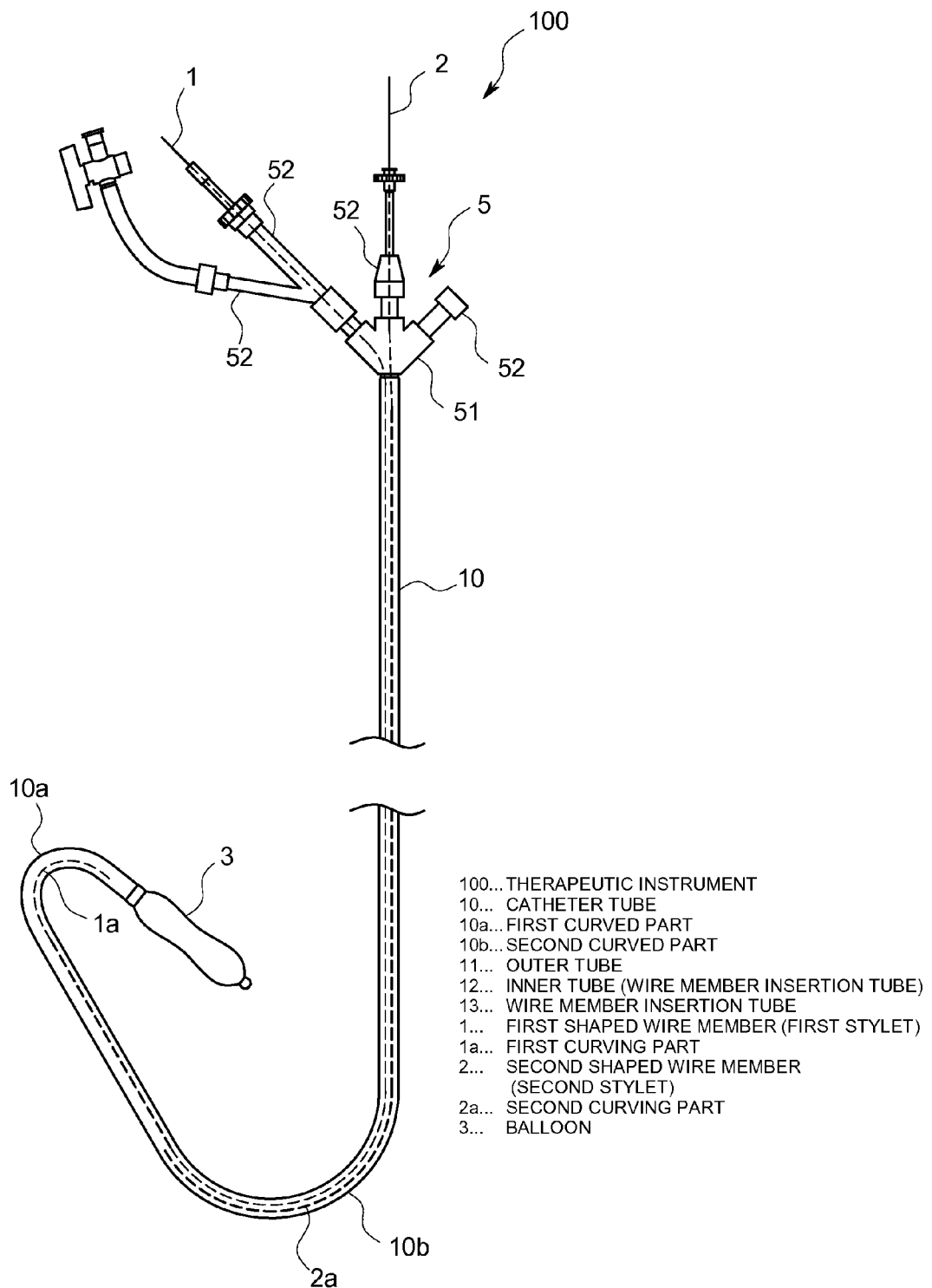
FIG. 1 is an overall view illustrating a therapeutic or diagnostic instrument in one embodiment of the present invention.

100 Therapeutic instrument (therapeutic or diagnostic instrument)

10 Catheter tube
10a First curved part
10b Second curved part
11 Outer tube
12 Inner tube (wire member insertion tube)
13 Wire member insertion tube
1 First shaped wire member (first stylet)
1a First curving part
2 Second shaped wire member (second stylet)
2a Second curving part
3 Balloon
4 Guide wire

DESCRIPTION OF EMBODIMENTS

One embodiment of the present invention is described with reference to drawings.

Figure 2:
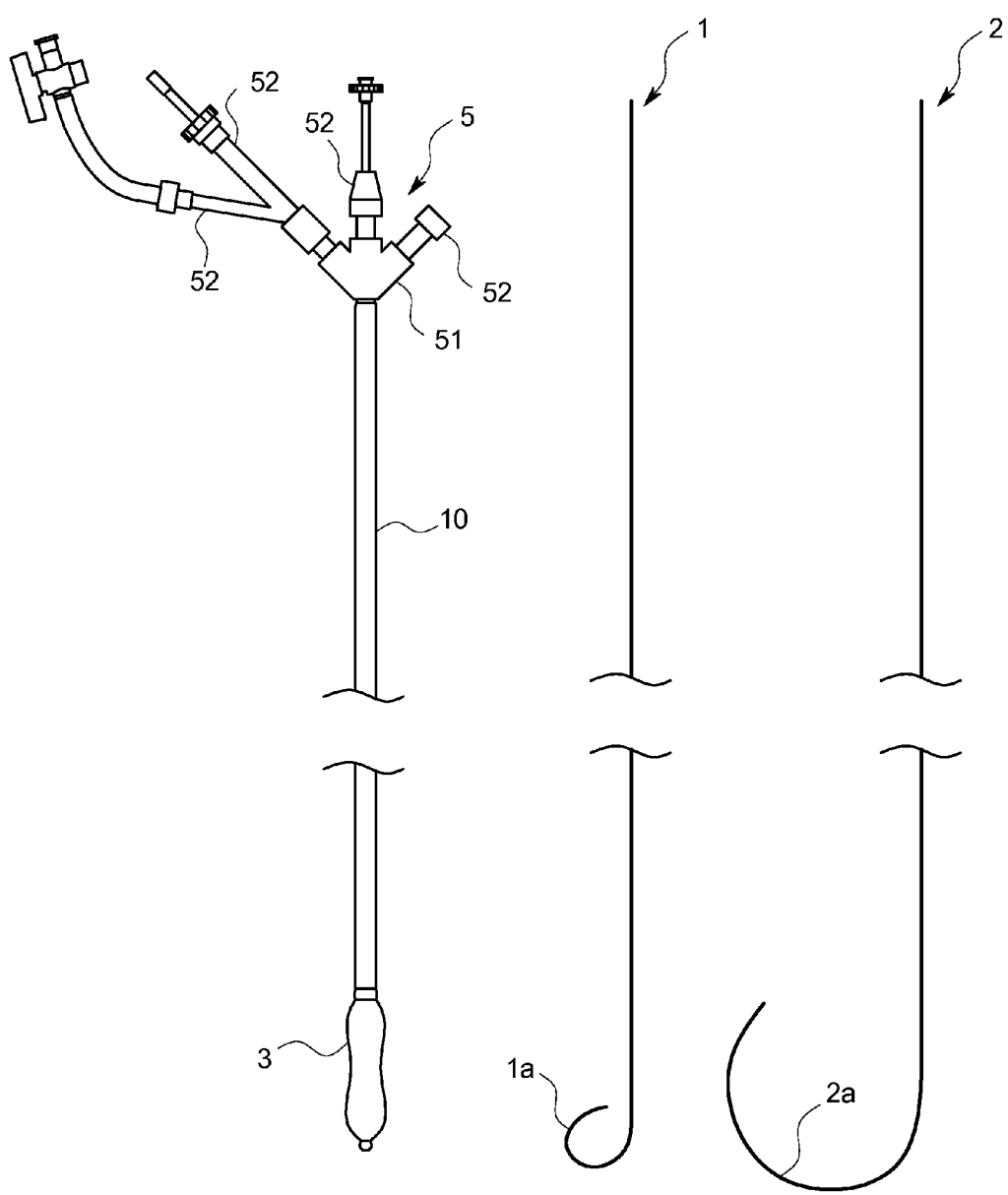
FIG. 2 is an exploded view illustrating the therapeutic or diagnostic instrument in the same embodiment.

A catheter-type therapeutic instrument 100 according to the present embodiment is one that, as illustrated in FIGS. 1 and 2, includes: a catheter tube 10; a balloon 3 attached to the fore end of the catheter tube 10; a ferrule member 5 attached to the base end of the catheter tube 10; and two types of shaped wire members 1 and 2 (hereinafter also referred to as a first stylet 1 and a second stylet 2) inserted into the catheter tube 10 and movable back and forth.

Figure 3:
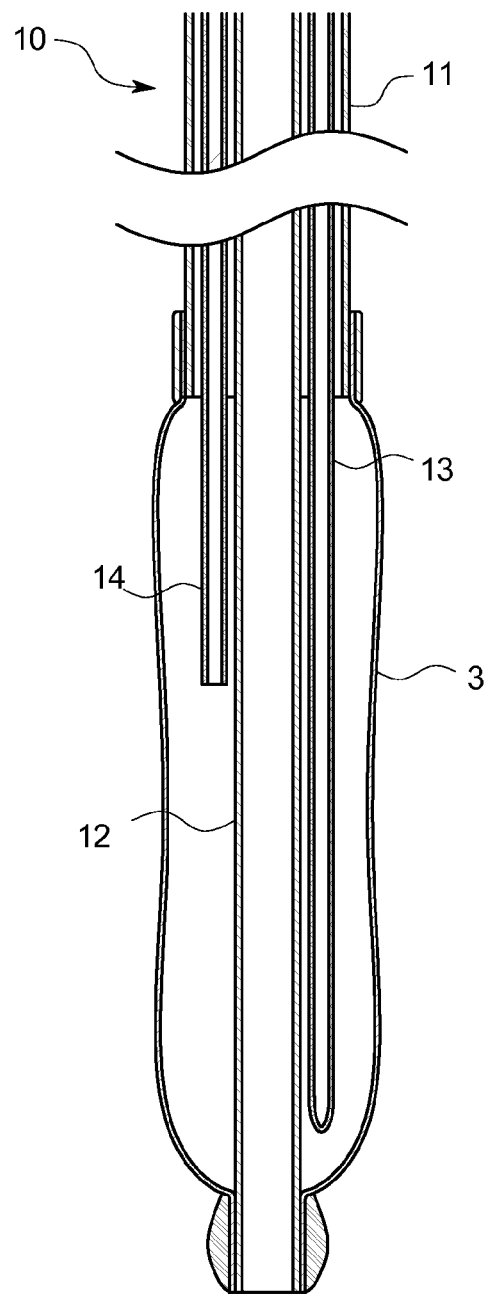
FIG. 3 is a longitudinal cross-sectional view illustrating the internal structure of a balloon and a catheter tube in the same embodiment.
Figure 4:
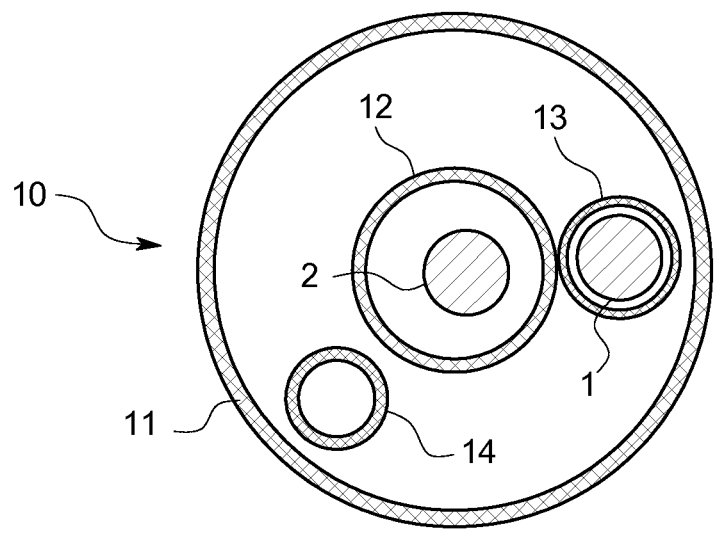
FIG. 4 is a transverse cross-sectional view illustrating the internal structure of the catheter tube in the same embodiment.

As illustrated in FIGS. 3 and 4, the catheter tube 10 is basically one having double tube structure that includes: an outer tube 11; and an inner tube 12 for inserting a guide wire 4; however, in the present embodiment, between the outer tube 11 and the inner tube 12, two tubes are additionally inserted. One is a drain tube 14 for removing air inside the balloon 3, and placed such that the fore end thereof opens inside the balloon 3. The other one is a wire member insertion tube 13 for inserting the first stylet 1, and the fore end thereof is sealed so as to prevent the stylets 1 and 2 inserted inside from protruding.

The balloon 3 is, particularly as illustrated in FIG. 3, mainly made of an elastic resin film (natural or synthetic resin), and attached so as to cover the fore end part of the outer tube 11. The inner tube 12 is provided so as to penetrate through the balloon 3, and the balloon 3 is configured to inflate in a straw bag shape in the case of pressing inflation liquid into a space between the outer tube 11 and the inner tube 12. Note that the balloon 3 in the present embodiment is a well-known one referred to as the Inoue balloon 3, of which the middle part is provided with an unillustrated beltlike body that slightly suppresses the middle part from inflating as compared with the other part. When the inflation liquid is pressed in, the beltlike body acts to first inflate the first half part and then inflate the second half part, and consequently the Inoue balloon 3 is formed in a straw bag shape.

As illustrated in drawings such as FIG. 1, the ferrule member 5 is one formed of a hard resin material, and includes: a base part 51 connected to the catheter tube 10; and a plurality of branch parts 52 branching from the base part 51. The respective branch parts 52 are adapted to be hollow, and configured to be communicatively connected to the inner tube 12, the space between the inner tube 12 and the outer tube 11, the drain tube 14, and the wire member insertion tube 13.

The stylets 1 and 2 are Nitinol or stainless steel ones that are substantially inelastic in their length directions but have a predetermined elastic restoring force against curving, and as illustrated in FIG. 2, on the tip sides thereof, respectively include curving parts 1a and 2a that curve in a natural state.

The degree of curvature is different between the curving part 1a (hereinafter also referred to as a first curving part 1a) of the first stylet 1 and the curving part 2a (hereinafter also referred to as a second curving part 2a) of the second stylet 2. Here, the degree of curvature of the first curving part 1a is configured to be higher than the degree of curvature of the second curving part 2a.

The rigidity of the stylets 1 and 2 against curving is set higher than that of the guide wire 4, and as illustrated in FIG. 1, the catheter tube 10 is configured such that, when inserting the stylets 1 and 2 into the catheter tube 10, sites corresponding to the curving parts 1a and 2a of the stylets 1 and 2 curve correspondingly to the degrees of curvature of the respective curving parts 1a and 2a to respectively form curved parts 10a and 10b.

More specifically, when inserting the two stylets 1 and 2 into the catheter tube 10, the catheter tube 10 is curved approximately 270 to 360 degrees as a whole by the first and second curving parts 1a and 2a. In particular, the degree of curvature of the catheter tube 10 caused by the first curving part 1a is preferably 150 to 180 degrees, making the catheter tube 10 face in the substantially opposite direction, and may be set so as to further curve the catheter tube 10 up to approximately 210 degrees.

Note that, although not illustrated, the tip parts of the stylets 1 and 2 are configured to be tapered to wind a thin wire, and also configured to be made more flexible than the other part to easily curve. This is to prevent an inner wall of a blood vessel or the like from being damaged even if any of the tip parts comes into contact with the inner wall. This is also to make the stylets 1 and 2 smoothly movable in the catheter tube.

Next, an example of a method for treating, for example, aortic valve stenosis using the therapeutic instrument 100 having a configuration as described above is described with reference to FIGS. 5 to 13.

Figure 5:
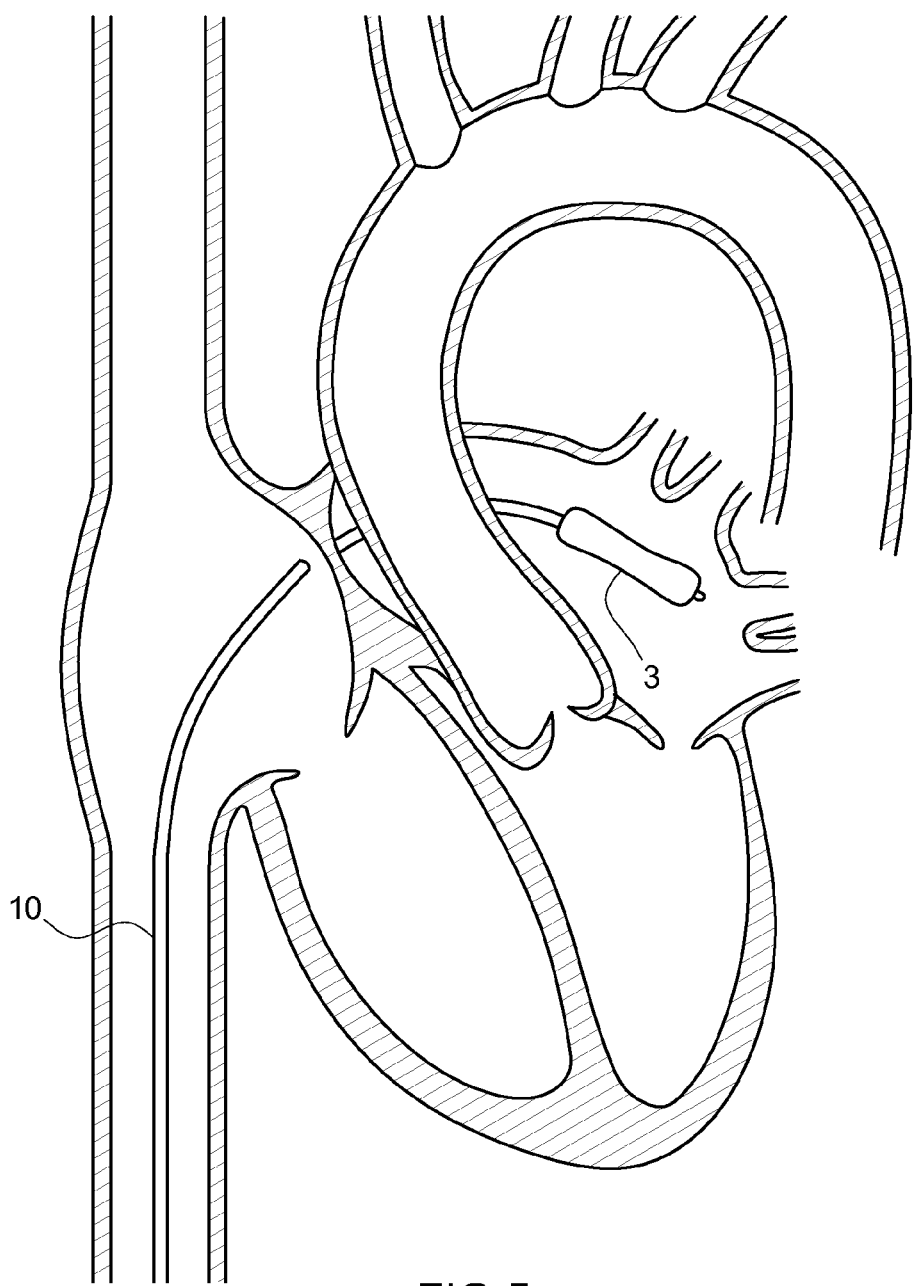
FIG. 5 is a method explanatory diagram illustrating a method for inserting the therapeutic or diagnostic instrument into the heart in the same embodiment.

First, as illustrated in FIG. 5, the balloon-equipped catheter tube 10 is inserted from, for example, the inferior vena cava, and the balloon 3 is made to penetrate through the interatrial septum from the right atrium and reach the left atrium. Note that to make the catheter tube 10 penetrate through the interatrial septum, interatrial transseptal puncture is used; however, this is an existing technique, and therefore description thereof is omitted.

Figure 6:
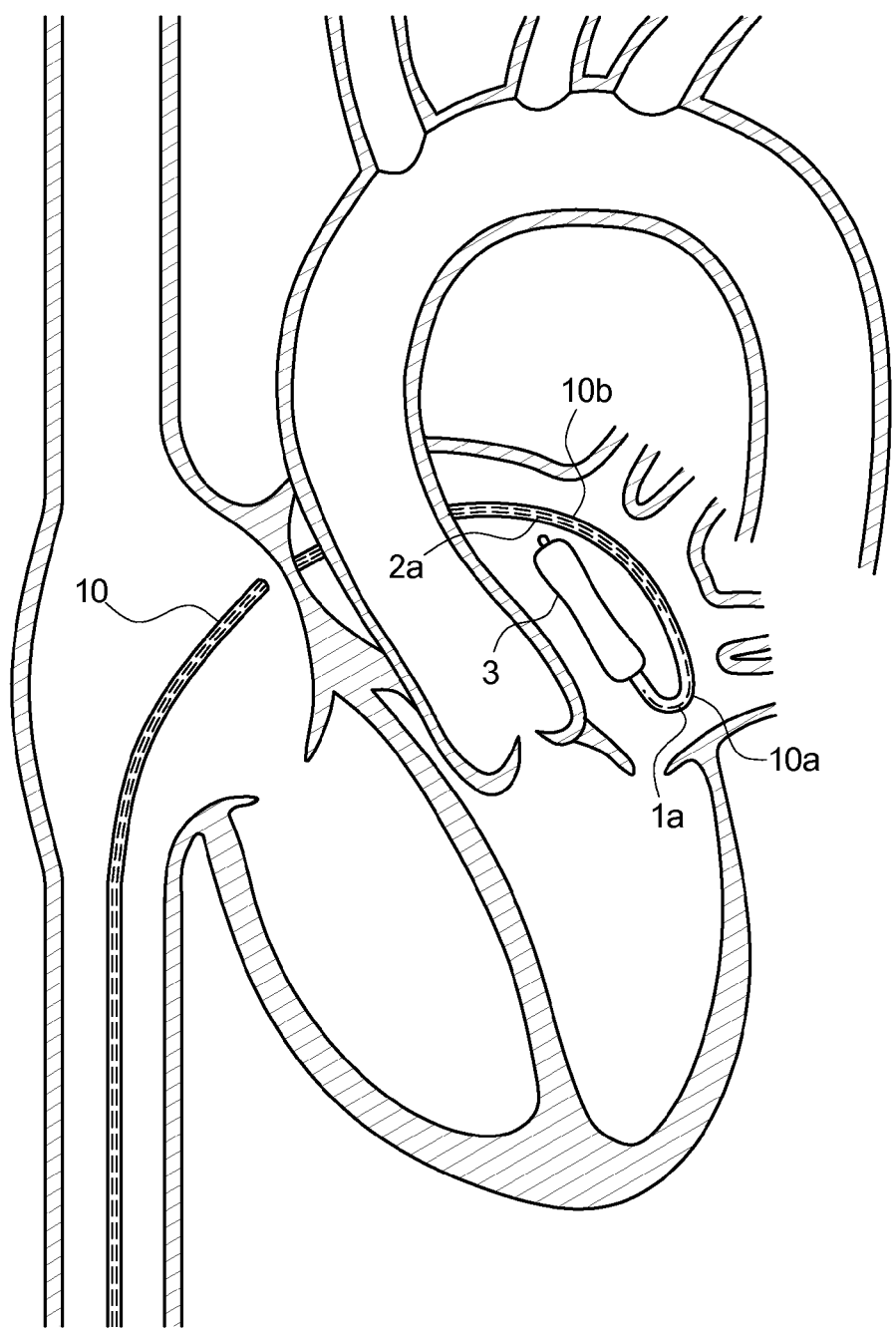
FIG. 6 is a method explanatory diagram illustrating the method for inserting the therapeutic or diagnostic instrument into the heart in the same embodiment.

Then, as illustrated in FIG. 6, the first stylet 1 and the second stylet 2 are respectively inserted into the wire member insertion tube 13 of the catheter tube 10 and into the inner tube 12 of the catheter tube 10 to make the respective curving parts 1a and 1b reach the left atrium. When doing this, the first and second stylets are operated so as to more deeply insert the first curving part 1a having a small curvature (tight curve) than the second curving part 2a, and position the first curved part 10a of the catheter tube 10, which is formed by the first curving part 1a, on the fore end side beyond the second curved part 10b of the catheter tube 10, which is formed by the second curving part 2a.

Also as illustrated in the same drawing, the fore end part of the catheter tube is formed in a J-shape in the left atrium to position the first curved part 10a furthest ahead.

Figure 7:
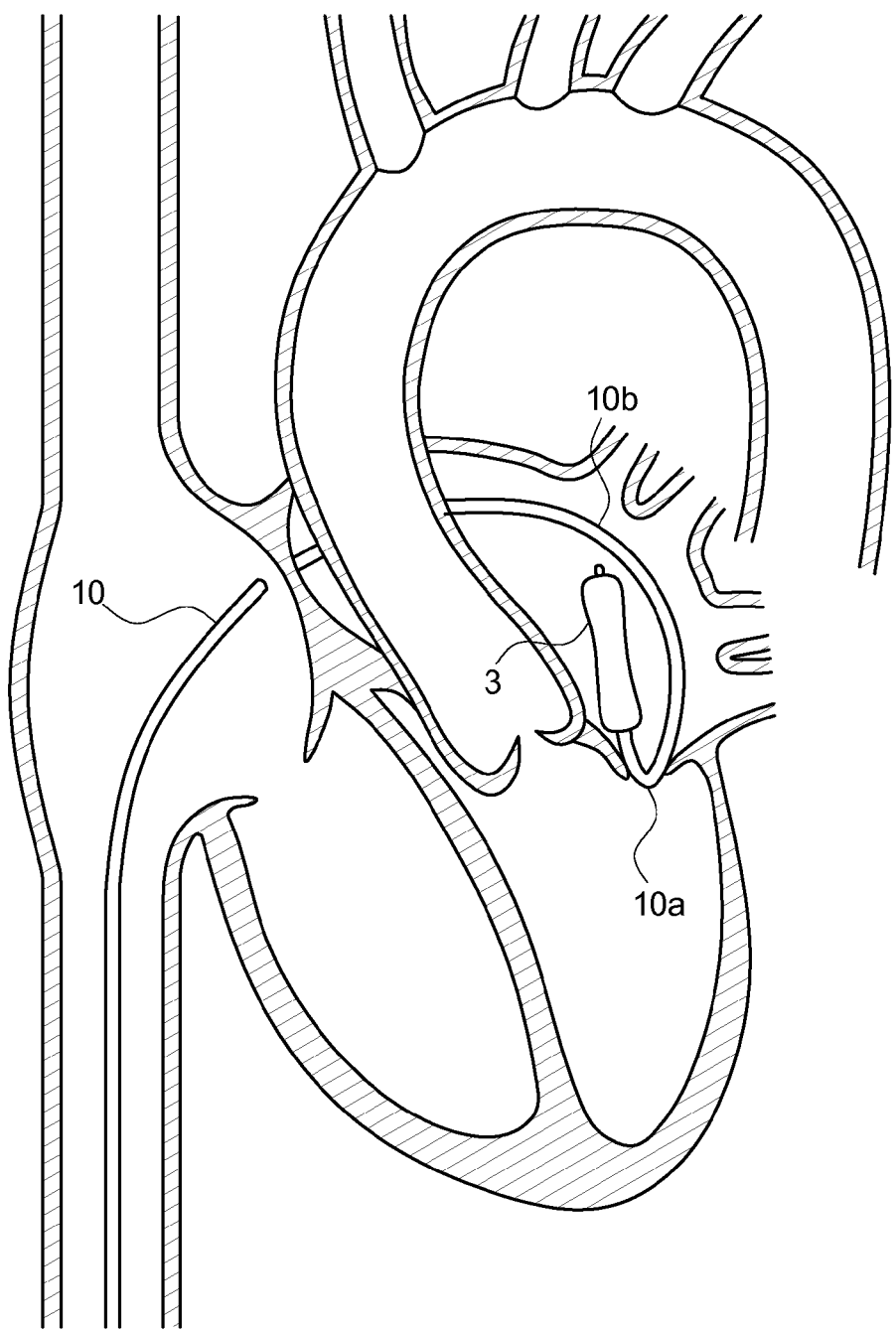
FIG. 7 is a method explanatory diagram illustrating the method for inserting the therapeutic or diagnostic instrument into the heart in the same embodiment.
Figure 8:
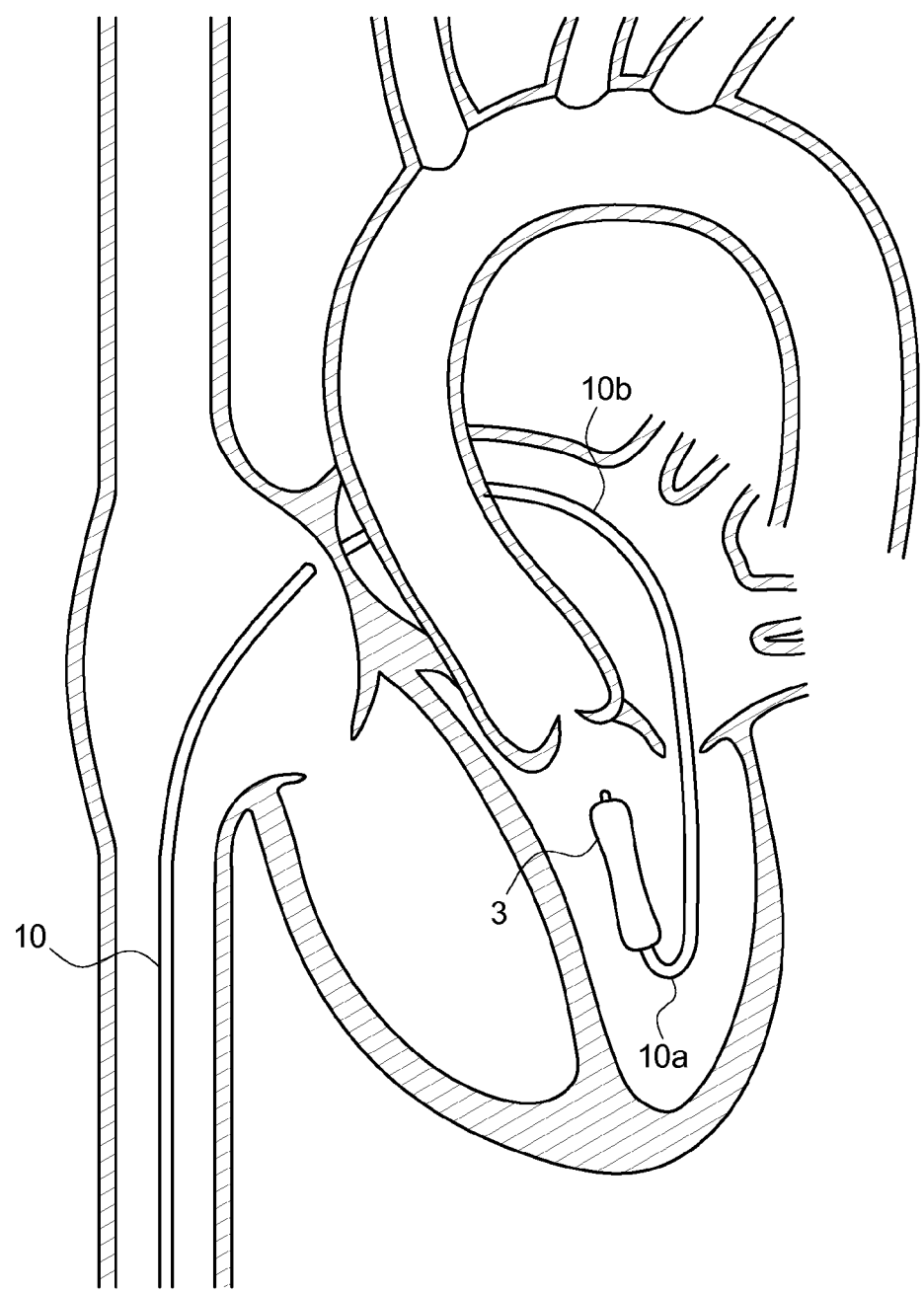
FIG. 8 is a method explanatory diagram illustrating the method for inserting the therapeutic or diagnostic instrument into the heart in the same embodiment.

Subsequently, as illustrated in FIG. 7, the catheter tube 10 is advanced together with the first stylet 1, and made to pass through the mitral valve from the first curved part 10a to make the balloon 3 reach the left ventricle. Note that illustrations after FIG. 7 are complicated and therefore illustrations of the stylets 1 and 2 are omitted. As a result, as illustrated in FIG. 8, the fore end of the balloon 3 (the fore end of the catheter tube 10) takes a position facing the aortic valve in the left ventricle.

Figure 9:
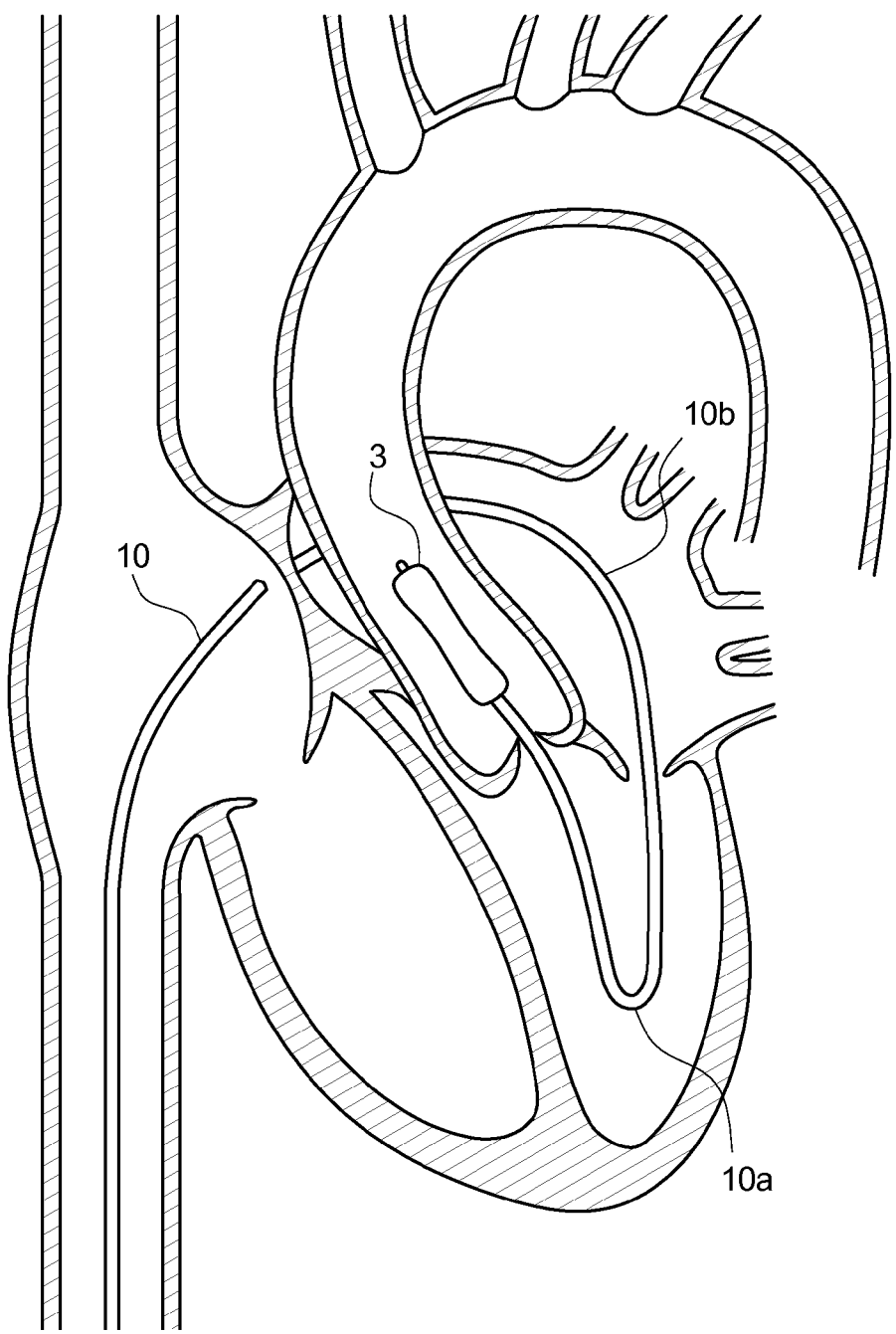
FIG. 9 is a method explanatory diagram illustrating the method for inserting the therapeutic or diagnostic instrument into the heart in the same embodiment.

After that, only the catheter tube 10 is further sent without moving the stylets 1 and 2. In doing so, the balloon 3 advances as if it were sucked toward the aortic valve through the bloodstream, and as illustrated in FIG. 9, passes through the aortic valve.

Figure 10:
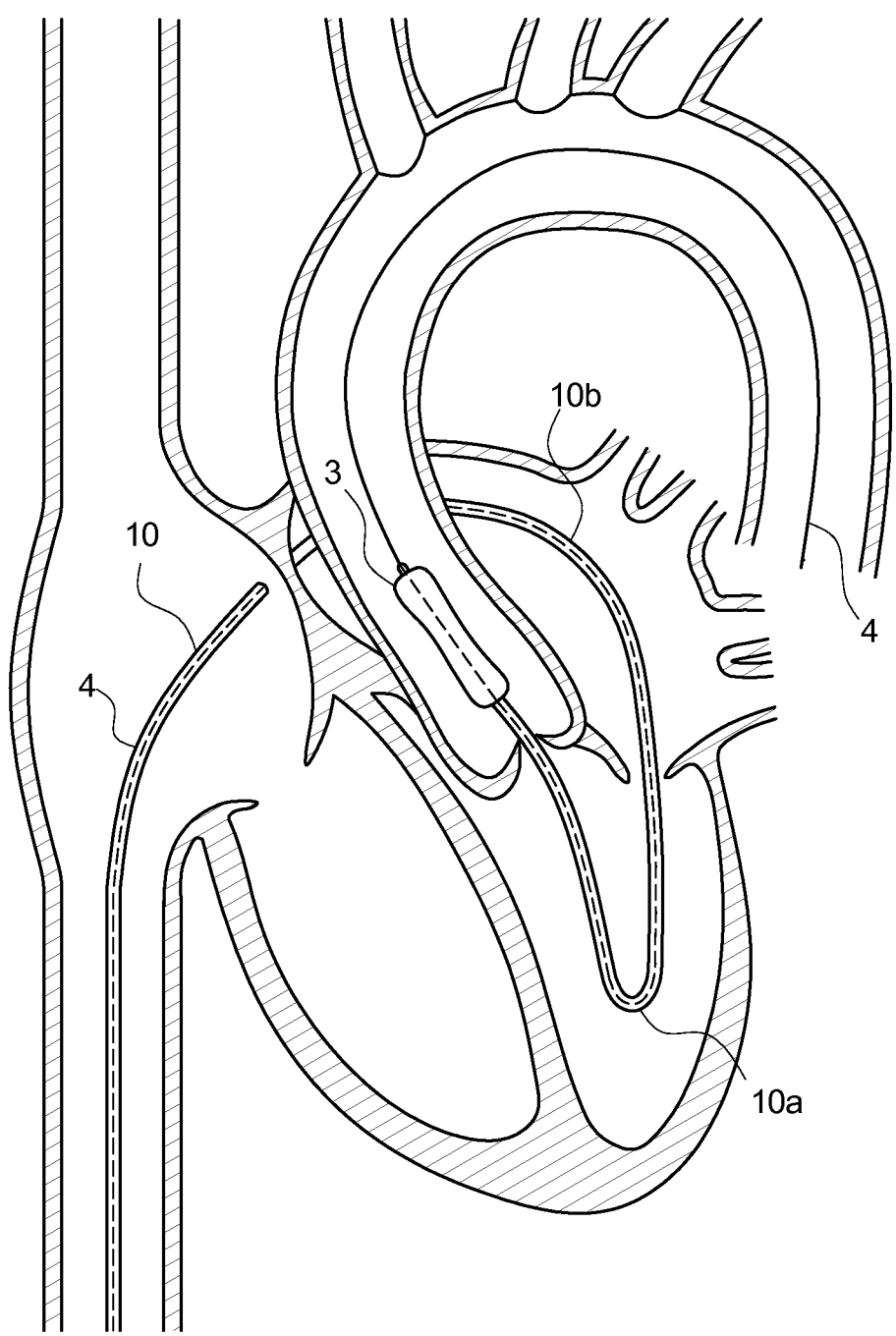
FIG. 10 is a method explanatory diagram illustrating the method for inserting the therapeutic or diagnostic instrument into the heart in the same embodiment.

In this state, in place of the second stylet 2, the guide wire 4 is inserted into the inner tube 12 and extended out of the fore end of the balloon 3, and as illustrated in FIG. 10, made to advance inside the aorta, and the fore end part of the guide wire 4 is made to reach the descending aorta. This stabilizes the catheter tube 10.

Figure 11:
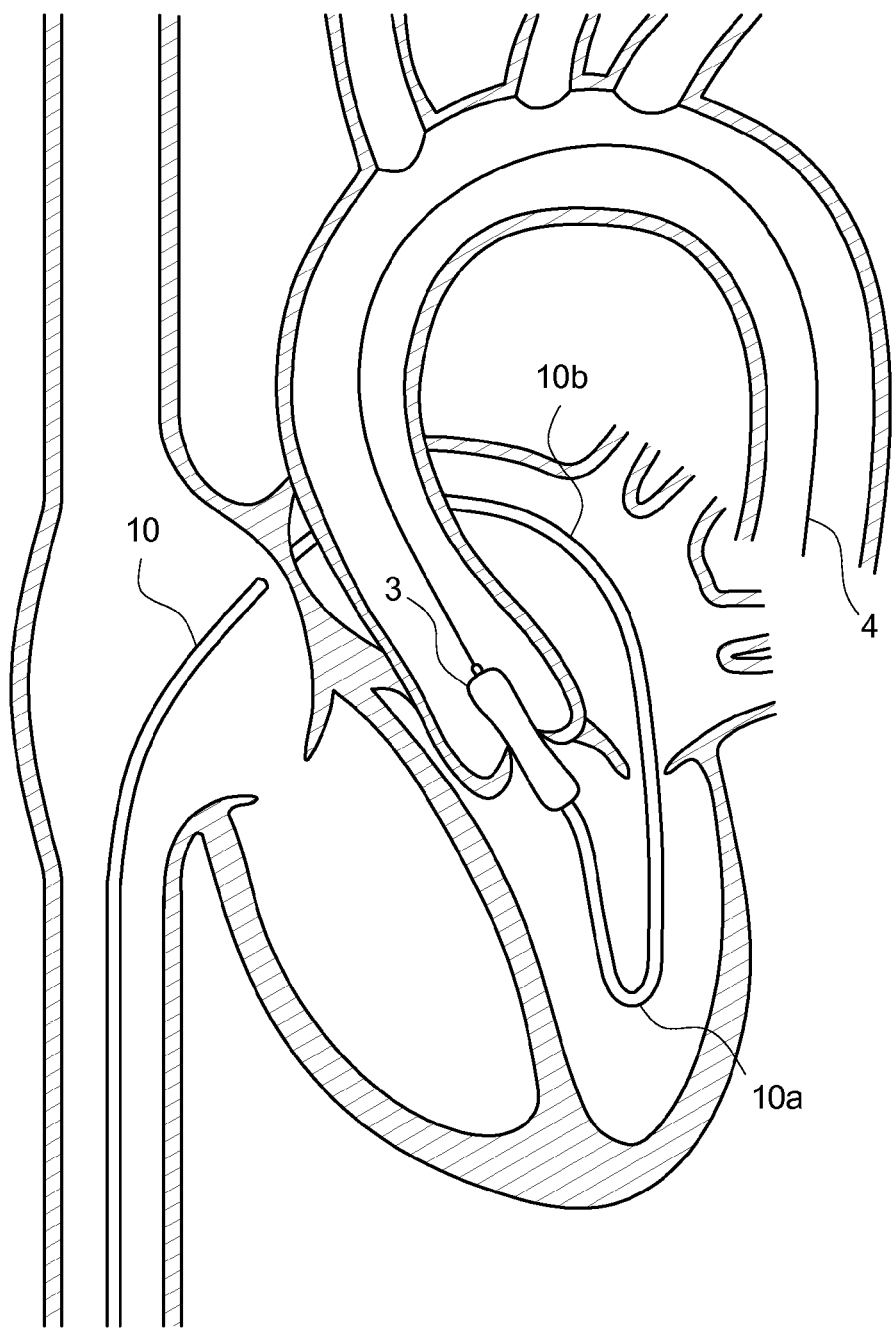
FIG. 11 is a method explanatory diagram illustrating the method for inserting the therapeutic or diagnostic instrument into the heart in the same embodiment.

Subsequently, as illustrated in FIG. 11, by slightly pulling back the catheter tube 10 while fixing the first stylet 1 in place, the balloon 3 is pulled back and positioned at the aortic valve. Alternatively, by slightly pushing in the first stylet 1 while fixing the base part of the catheter tube 10 in place, the balloon 3 can be pulled back. Note that in drawings after FIG. 11, illustrating the guide wire 4 inside the catheter tube 10 is omitted.

Figure 12:
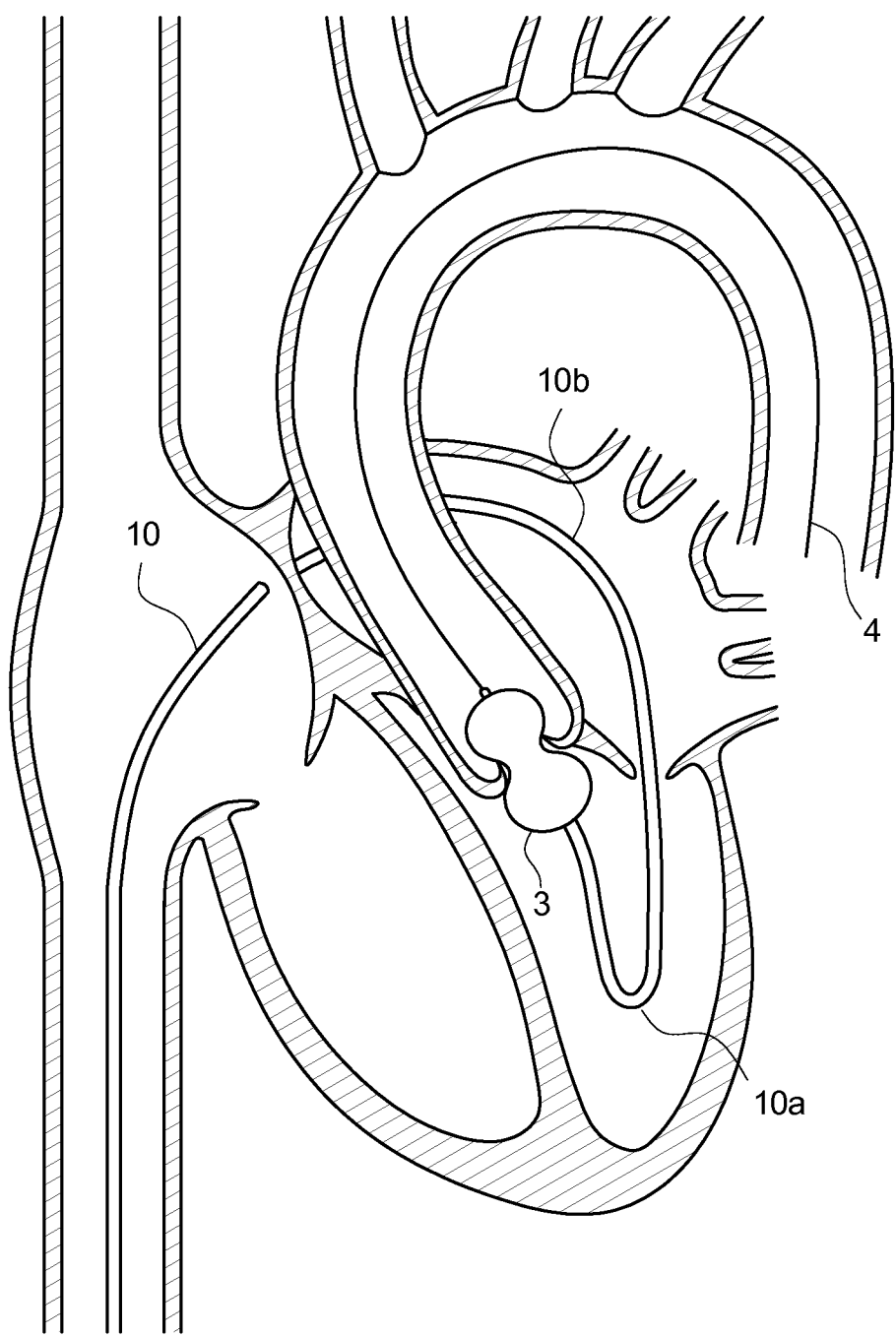
FIG. 12 is a method explanatory diagram illustrating the method for inserting the therapeutic or diagnostic instrument into the heart in the same embodiment.
Figure 13:
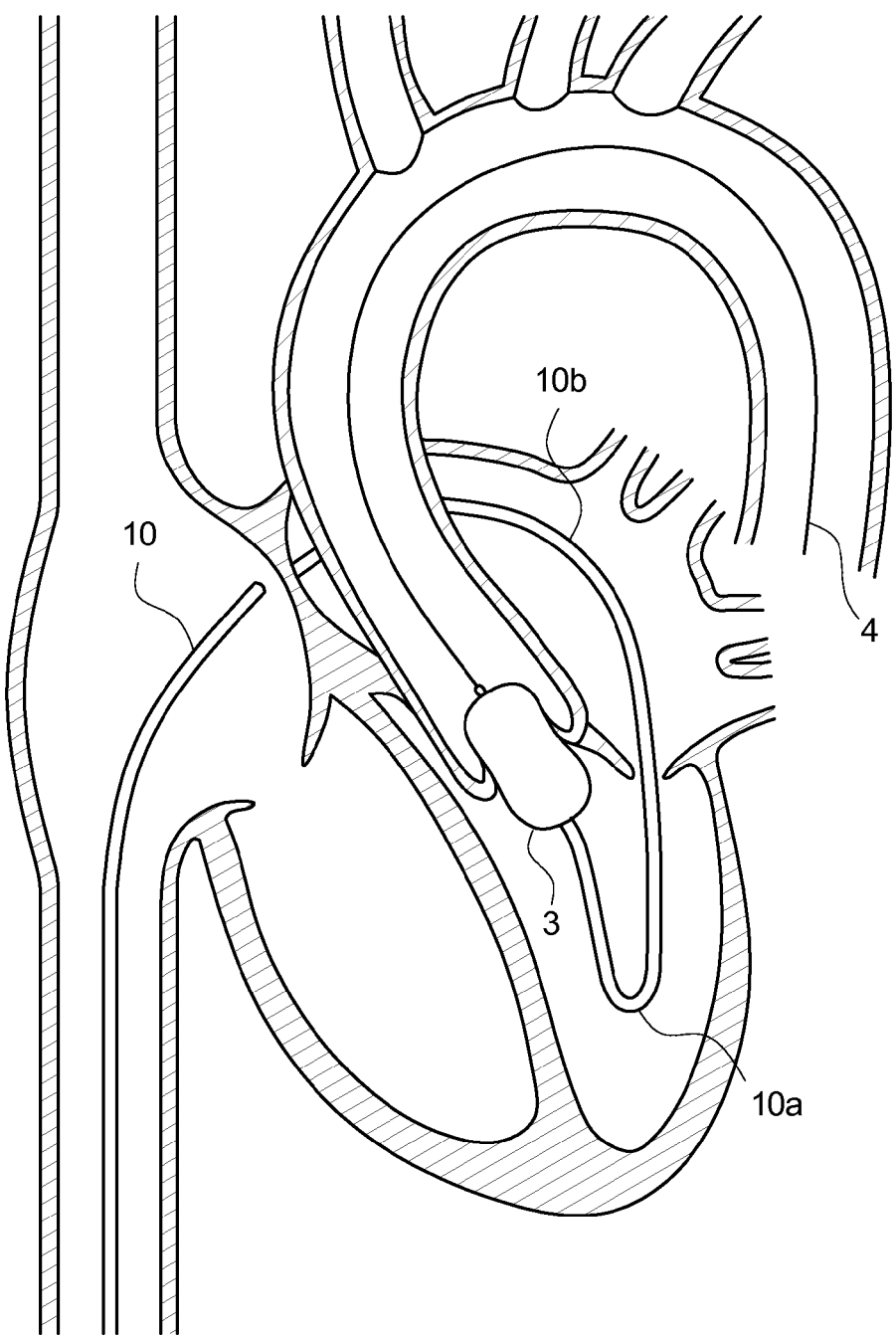
FIG. 13 is a method explanatory diagram illustrating the method for inserting the therapeutic or diagnostic instrument into the heart in the same embodiment.

Then, as illustrated in FIG. 12, after the inflation liquid has been pressed in to inflate only the first half part of the balloon 3, the balloon 3 is more accurately positioned using the first half part as an anchor, and then the inflation liquid is further pressed in to also inflate the second half part of the balloon 3, whereby a stenosis site of the aortic valve is spread out. When doing this, the balloon 3 is not inflated to the maximum diameter at once, but may be repeatedly inflated and deflated to increase an inflation diameter stepwise.

After the stenosis site has been treated, the balloon 3 is deflated, and then the guide wire is pulled out. Then, only the catheter tube 10 is moved back without moving the first stylet 1. In doing so, the balloon 3 separates from the aortic valve and returns into the left ventricle, coming into the state illustrated in FIG. 8.

Figure 14:
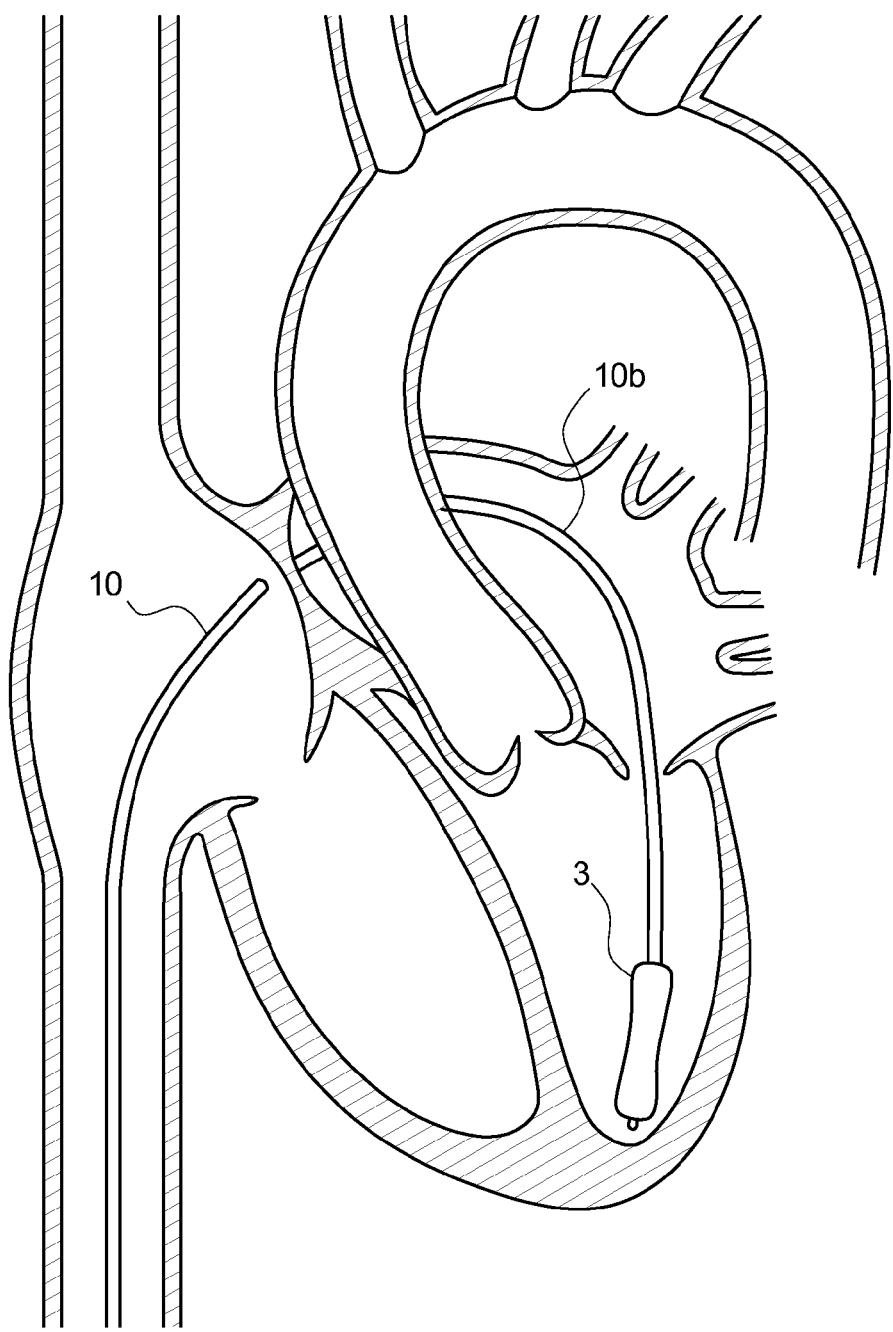
FIG. 14 is a method explanatory diagram illustrating the method for inserting the therapeutic or diagnostic instrument into the heart in the same embodiment.

Subsequently, as illustrated in FIG. 14, after the first stylet 1 has been pulled out to release the first curved part 10a, the catheter tube 10 is pulled out of the body.

In addition, it goes without saying that in the operations described above, the catheter tube 10 and stylets 1 and 2 may be subtly moved in order to correct a deviation caused by the heart movements.

As described above, such an instrument makes it possible to curve the catheter tube 10 at desired sites and make the balloon 3 easily reach the aortic valve only by operating the two stylets 1 and 2. The point is, in particular, to make the catheter tube 10 pass through the mitral valve leading not with the balloon 3, but with the first curved part 10a, which is preliminarily curved such that the balloon 3 faces the aortic valve, being at the head, and by performing operations in this manner, the catheter tube 10 is never curved in the left ventricle having a relatively small volume, making surgical operations extremely easy.

Also, the balloon 3 is stabilized at the aortic valve by the guide wire 4; however, the guide wire 4 is inserted, guided by the catheter tube 10, contrary to the conventional manner, and therefore the need for a complicated and difficult operation of looping the guide wire 4 360 degrees in the heart is eliminated.

Further, the stylets 1 and 2 keep the looping shape of the catheter tube 10, and therefore the catheter tube 10 can be easily and reasonably removed from the aortic valve.

Note that the present invention is not limited to the above-described embodiment.

For example, the guide wire 4 for fixation is not necessarily required.

Also, the tube inside which the catheter tube is inserted with each stylet can be variously changed. For example, in the above-described embodiment, the first stylet is inserted into the wire member insertion tube; however, the present invention may be adapted to make the inner tube also serve as the wire member insertion tube, and insert the two stylets, i.e., the first and second stylets, into the inner tube. Also, between the outer tube and the inner tube, the two stylets may be inserted to make the inner tube serve as a dedicated tube for inserting the guide wire. In such a case, in order to insert the respective stylets, two wire member insertion tubes may be provided. In doing so, the need for work to remove the stylet when inserting the guide wire is eliminated.

Figure 15:
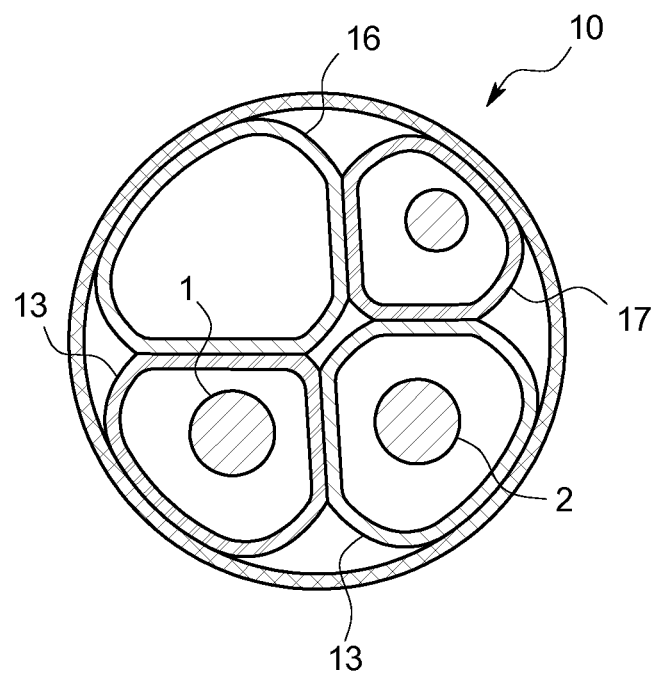
FIG. 15 is a transverse cross-sectional view illustrating the internal structure of a catheter tube in another embodiment of the present invention.

The catheter tube may also be, without limitation to the double tube, adapted such that as illustrated in FIG. 15, for example, an inflation liquid introduction tube 16, a guide wire insertion tube 17, wire member insertion tubes 13, and the like are provided together.

To insert the catheter tube 10 into the aortic valve from the left ventricle, there is also a method that moves back the first stylet 1.

Figure 16:
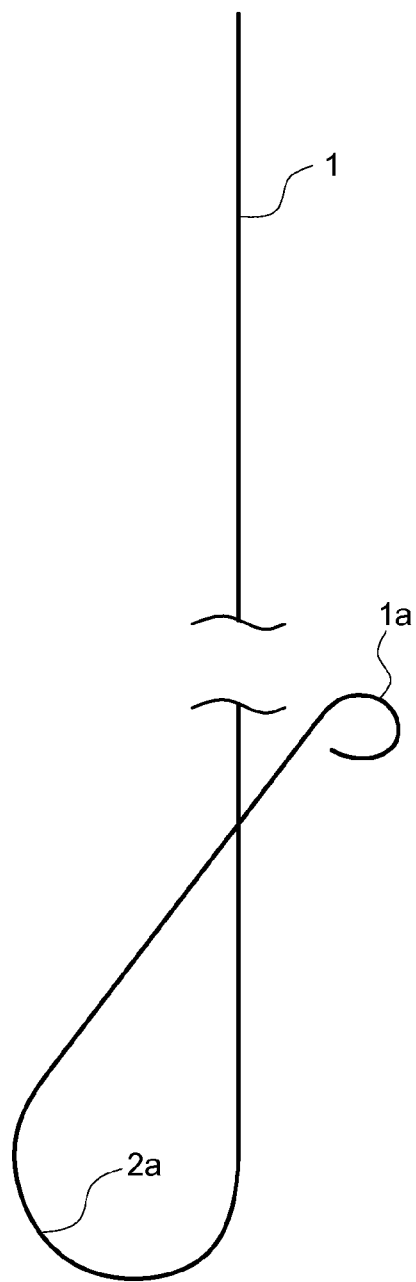
FIG. 16 is a diagram illustrating a stylet in still another embodiment of the present invention.

Three or more stylets may be used, and as illustrated in FIG. 16, only one stylet having two or more curving parts 1a and 2a may be used.

In order to make the movement of the stylets smoother, a branching angle between the branch parts 52 and shapes of the branch parts 52 may be gentler than that in FIG. 1 and curved, respectively.

Figure 17:
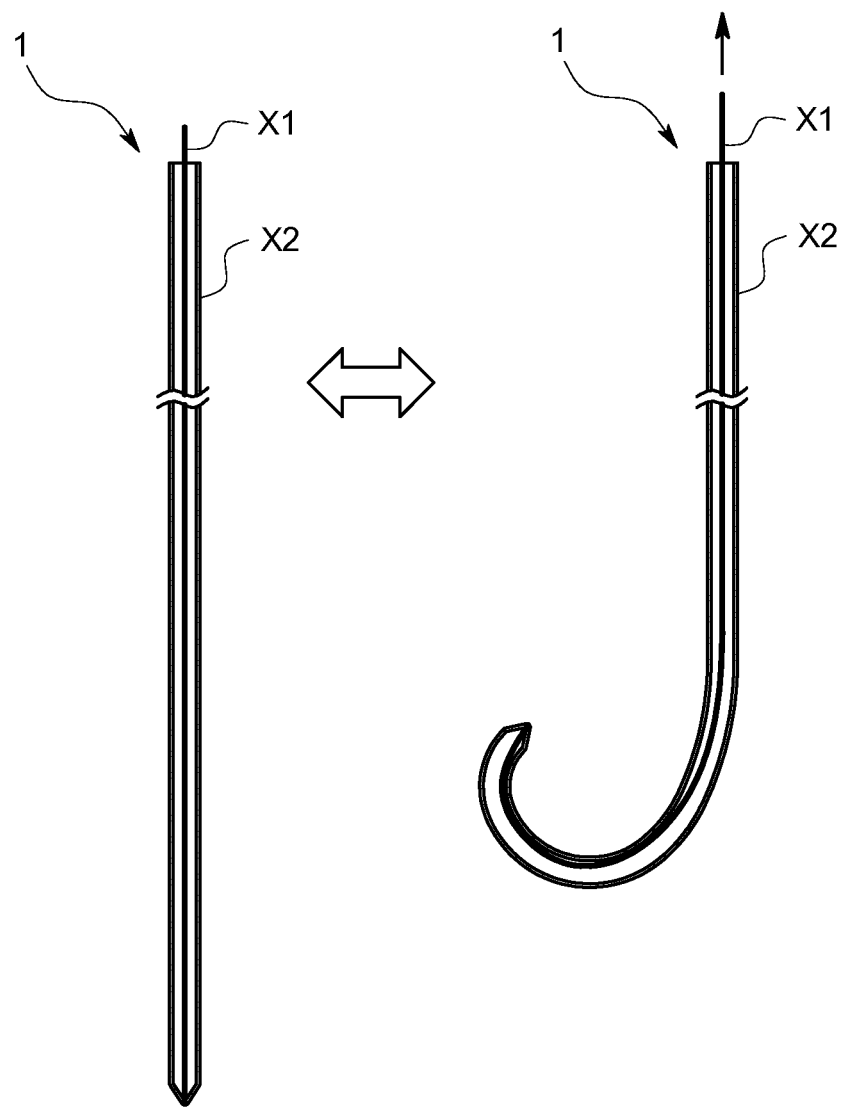
FIG. 17 is a diagram illustrating a stylet in yet another embodiment of the present invention.

Also, for example, the degree of curvature of at least one or both of the first stylet and the second stylet may be adapted to be changeable with an operation performed by hand at the rear end of the catheter tube. Specifically, an example where, as illustrated in FIG. 17, the first stylet 1 includes a core material X1 and a flexible tube (a coil or the like is also possible) X2 arranged around the core material X1, and the tip of the core material X1 is joined to the fore end of the flexible tube X2 can be cited. Given such a configuration, by pulling the core material X1 by hand at the rear end of the catheter tube, the first stylet 1 can be curved correspondingly to a pulled distance. Such a configuration makes it possible to expand an applicable scope to therapies and diagnoses of various sites as well as further improving operability.

Note that preferably, the first curving part in this case is not at a fixed position but adapted to be changeable by an operation at hand performed by hand at the rear end of the catheter tube.

What is attached to the fore end of the catheter tube is not only the balloon but may also be, for example, a prosthetic valve, stent graft, stent, filter, or the like. To replace the aortic valve by a prosthetic valve, a surgical operation that approaches from the femoral artery, the left ventricular apex, or the like to implant the prosthetic valve in the aorta through a catheter has been performed; however, according to the present invention, a surgical operation using an antegrade approach also becomes possible.

The advantages of a transvenous approach are described below. In the case of advancing a therapeutic catheter tube (relatively large and hard) through the femoral artery to the aortic valve beyond the aortic arch, there is a risk of detaching a sclerotic lesion, a thrombus, or the like in the aortic wall, which then flows into a cerebral blood vessel to cause a cerebral infarction. On the other hand, in a method that reaches the aortic valve in a manner through the femoral vein (through the inferior vena cava), such a risk is extremely low. Also, the approach through the femoral artery requires an incisional operation for exposing the femoral artery in order to insert the catheter tube; however, the approach through the femoral vein does not require an incisional operation because a catheter tube is inserted into the vein using a puncture, i.e., the catheter is percutaneously insertable. In the case where a catheter tube is relatively small, even in the case of an approach through the femoral artery, the catheter tube can be inserted into the femoral artery using a puncture; however, after the catheter tube has been removed postoperatively, astriction is required for a long period of time, and if the astriction is insufficient, severe hemorrhaging may occur. On the other hand, postoperative astriction is completed in a short period of time after a similar catheter tube has been inserted into the femoral vein using a puncture. Accordingly, the patient's suffering, surgical time, and postoperative rest time are considerably reduced. Furthermore, in the case of the elderly, the femoral artery is often associated with stenosis or bending caused by an arteriosclerotic lesion, and a catheter tube cannot be inserted or, at the time of insertion, a complication such as vascular injury or occlusion occurs. The method through the vein has no such troublesome problems at all.

By applying the method of the present invention in consideration of the above-described advantages, a catheter tube can be easily, safely, transvenously and antegradely inserted into each of the heart, aortic valve, coronary arteries, the aorta and all of its branching blood vessels, carotid arteries, cerebral blood vessels, and the like, and correspondingly catheterization can be transvenously and antegradely performed. This is considered to open up a new vista for future catheterization, and make significant contributions to the development of catheterization.

The catheter-type therapeutic instrument having stylets has been described; however, the present invention can also be applied to a catheter-type diagnostic instrument such as one in which the fore end of a catheter tube is attached with an endoscope or an ultrasonic device. In addition, injecting a contrast material through a through-hole of a catheter to obtain Inoue findings from X-ray fluoroscopy is an important diagnostic method.

Further, the present invention can be applied not only to cardiac blood vessels but also to other sites.

Besides, the present invention can be variously modified without departing from the scope thereof.

The invention claimed is:

1. A therapeutic or diagnostic instrument comprising a catheter tube to be inserted into a body, and at least two shaped wire members having predetermined bending elasticity, wherein:

among the shaped wire members, a first shaped wire member has a first curving part that curves in a natural state, and when inserted into the catheter tube, curves the catheter tube correspondingly with the first curving part;

a second shaped wire member has a second curving part that curves in the natural state, and when inserted into the catheter tube, curves the catheter tube correspondingly with the second curving part;

the catheter tube has a double tube structure having an outer tube and an inner tube for inserting a guide wire;

the first shaped wire member is inserted between the outer tube and the inner tube;

the second shaped wire member is inserted into the inner tube; and a wire member insertion tube of which a fore end is sealed is placed between the outer tube and the inner tube, and the first shaped wire member is inserted into the wire member insertion tube.

2. A therapeutic or diagnostic instrument insertion method that inserts a therapeutic or diagnostic instrument into a cardiac blood vessel, the therapeutic or diagnostic instrument comprising a catheter tube to be inserted into a body, and at least two shaped wire members having predetermined bending elasticity, wherein:

among the shaped wire members, a first shaped wire member has a first curving part that curves in a natural state, and when inserted into the catheter tube, curves the catheter tube correspondingly with the first curving part;

a second shaped wire member has a second curving part that curves in the natural state, and when inserted into the catheter tube, curves the catheter tube correspondingly with the second curving part; and the therapeutic or diagnostic instrument insertion method, comprising:

(1) making a fore end part of the catheter tube penetrate through an interatrial septum from a right atrium and reach a left atrium;

(2) inserting the first shaped wire member and the second shaped wire member into the catheter tube to form a first curved part at the fore end part of the catheter tube with the first curving part as well as forming a second curved part on a base end side beyond the first curved part of the catheter tube with the second curving part, the second curved part being curved more gently than the first curved part;

(3) advancing the catheter tube, and making the catheter tube pass through a mitral valve with the first curved part being at a head and reach a left ventricle in a substantially unchanged position; and (4) advancing the catheter tube, and making the catheter tube pass through an aortic valve from the fore end part of the catheter tube.

* * * * *